(12) United States Patent
Wimberger-Friedl et al.

(10) Patent No.: US 12,014,492 B2
(45) Date of Patent: Jun. 18, 2024

(54) CHARACTERIZING LESIONS IN RADIOLOGY IMAGES

(71) Applicant: KONINKLIJKE PHILIPS N.V., Eindhoven (NL)

(72) Inventors: Reinhold Wimberger-Friedl, Waalre (NL); Marinus Bastiaan Van Leeuwen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 314 days.

(21) Appl. No.: 17/293,540

(22) PCT Filed: Nov. 11, 2019

(86) PCT No.: PCT/EP2019/080775
§ 371 (c)(1),
(2) Date: May 13, 2021

(87) PCT Pub. No.: WO2020/104223
PCT Pub. Date: May 28, 2020

(65) Prior Publication Data
US 2022/0028064 A1    Jan. 27, 2022

(30) Foreign Application Priority Data
Nov. 19, 2018    (EP) .................................... 18206936

(51) Int. Cl.
*G06T 7/00* (2017.01)
*G06V 10/75* (2022.01)
(Continued)

(52) U.S. Cl.
CPC .......... *G06T 7/0012* (2013.01); *G06V 10/751* (2022.01); *G06V 10/803* (2022.01);
(Continued)

(58) Field of Classification Search
CPC ..................... G06T 7/0012; G06T 7/00; G06T 2207/10116; G06T 2207/20081;
(Continued)

(56) References Cited

U.S. PATENT DOCUMENTS 9,798,856 B2    10/2017   Banerjee et al.
9,858,665 B2    1/2018    Metzger et al.
(Continued)

FOREIGN PATENT DOCUMENTS

WO    2016040784 A1    3/2016

OTHER PUBLICATIONS

PCT/EP2019/080775, ISR & WO, Feb. 3, 2020, 24 Page Document.
(Continued)

*Primary Examiner* — Tuan H Nguyen
(74) *Attorney, Agent, or Firm* — Sherry Austin (57) ABSTRACT

The invention relates to a method for use in characterizing lesions in radiology images, comprising performing a computer-based analysis of a pathology image of a sample of a lesion of a subject in order to recognize tissue and/or cellular characteristics of the lesion, wherein the analysis produces a derived pathology image that represents the recognized tissue and/or cellular characteristics, computing one or more radiology features for the lesion from a radiology image of the lesion, and determining correlations between the computed one or more radiology features and the recognized tissue and/or cellular characteristics. With this method, biological ground truth information can be used to identify radiology features that are indicative of certain tissue and/or cellular characteristics of lesions and that may therefore be better suited for characterizing the lesions. Such radiology features can then be used together with the corresponding correlations for an improved characterization of lesions in radiology images.

18 Claims, 7 Drawing Sheets

(51) Int. Cl.
G06V 10/80 (2022.01)
G06V 10/82 (2022.01)
G06V 20/69 (2022.01)
G16H 70/60 (2018.01)

(52) U.S. Cl.
CPC ............ G06V 10/82 (2022.01); G06V 20/698 (2022.01); G16H 70/60 (2018.01); G06T 2207/10116 (2013.01); G06T 2207/20081 (2013.01); G06T 2207/20084 (2013.01); G06T 2207/30096 (2013.01)

(58) Field of Classification Search
CPC ........... G06T 2207/20084; G06T 2207/30096; G16H 70/60; G06V 20/698; G06V 10/751; G06V 10/803; G06V 10/82
See application file for complete search history.

(56) References Cited

U.S. PATENT DOCUMENTS

| 2006/0252025 | A1* | 11/2006 | Nitta | G01N 1/31 435/40.5 |
|---|---|---|---|---|
| 2014/0314292 | A1 | 10/2014 | Kamen et al. | |
| 2017/0053090 | A1 | 2/2017 | Viswanath et al. | |
| 2018/0012356 | A1* | 1/2018 | Madabhushi | G06T 7/0012 |

OTHER PUBLICATIONS

Aerts et al: "Decoding Tumour Phenotype by Noninvasive Imaging Using a Quantitative Radiomics Approach"; Nature Communications, 2011.
Lambin et al: "Radiomics:Extracting More Information From Medical Images Using Advanced Feature Analysis"; European Journal of Cancer 48 (4):441-446.
Kumar et al: "Radiomics:The Process and the Challenges"; Magnetic Resonance Imaging, 30 (9): 1234-1248, 2012.
Gillies et al: "Radiomics: Images Are More Than Pictures, They Are Data"; Radiology, 278 (2): 563-577, Feb. 2016.
Amadasun et al:"Texural Features Corresponding to Texural Properties"; IEEE Transactions on Systems, Man, and Cybernetics, vol. 19, No. 5, Sep./Oct. 1989, pp. 1264-1274.
Chicklore et al: "Quantifying Tumour Heterogeneity in F-FDG PET/CT Imaging by Texture Analysis"; Eur J Nucl Med Mol Imaging (2013) 40:133-140.
Cook et al: "Radiomics in PET:Principles and Applications"; Clin Transl Imaging (2014) 2:269-276.
Biomedical Texture Analysis:Fundamentals, Tools and Challenges; 1st Edition, Editors: Adrien Depeursinge, Omar S. Al-Kadi, Joseph Ross Mitchell; Aug. 2017.
Galloway: "Texture Analysis Using Gray Level Run Lengths"; Computer Graphics and Image Processing 4, pp. 172-179 (1975).
Gu et al: "Automated Delineation of Lung Tumors From CT Images Using a Single Click Ensemble Segmentation Approach"; Pattern Recognition 46 (2013)pp. 692-702.
Haralick et al: "Textural Features for Image Classification"; IEEE Transactions on Systems, Man and Cybernetics, vol. SMC-3, No. 6, Nov. 1973, pp. 610-621.
Heindl et al: "Mapping Spatial Heterogeneity in the Tumor Microenvironment:a New Era for Digital Pathology"; Laboratory Investigation (2015) 95, pp. 377-384.
Kwak et al: "Prostate Cancer: a Correlative Study of Multiparametric MR Imaging and Digital Histopathology"; Radiology, vol. 285, No. 1, Oct. 2017, pp. 147-156.
Parekh et al: "Radiomics:a New Application From Established Techniques"; Expert Review of Precision Medicine and Drug Development>Personalized Medicine in Drug Development and Clinical Practice, vol. 1, Issue 2, 2016, 5 Page Article.
Parmar et al: Radiomic Feature Clusters and Prognostic Signatures Specific for Lung and Head & Neck Cancer; Nature:Scientific Reports, Jun. 2015, 10 Page Document.
Pentland:"Fractal-Based Description of Natural Scenes"; IEEE Transactions on Pattern Analysis and Machine Intelligence, PAMI-6(6), pp. 661-674.
Thibault et al: "Advanced Statistical Matrices for Texture Characterization:Application to Cell Classification"; IEEE Transactions on Biomedical Engineering, vol. 61, No. 3, Mar. 2014, pp. 630-637.
Velasquez et al: "Volumetric CT-Based Segmentation of NSCLC Using 3-D Slicer"; Scientific Reports, vol. 3:3529, Dec. 2013.
Yip et al: "Use of Registration-Based Contour Propagation in Texture Analysis for Esophageal Cancer Pathologic Response Prediction"; Physics in Medicine & Biology, 61, 2016, pp. R150-R166.
Vaida et al., "RaPtomics-Integrating Radiomic and Pathomic Features for Predicting Recurrence in Early Stage Lung Cancer", Proc. of SPIE, vol. 10581 pp. 105810M-1-11, (2018).

* cited by examiner

FIG. 5

CHARACTERIZING LESIONS IN RADIOLOGY IMAGES

CROSS-REFERENCE TO PRIOR APPLICATIONS

This application is the U.S. National Phase application under 35 U.S.C. § 371 of International Application No. PCT/EP2019/080775, filed on Nov. 11, 2019, which claims the benefit of European Patent Application No. 18206936.9, filed on Nov. 19, 2018. These applications are hereby incorporated by reference herein.

FIELD OF THE INVENTION

The invention relates to a method, apparatus and computer program for use in characterizing lesions in radiology images.

BACKGROUND OF THE INVENTION

Cancer is one of the leading causes of morbidity and mortality worldwide; in 2015, it was responsible for 8.8 million deaths globally. In the diagnosis and monitoring of cancer, non-invasive radiology imaging, such as X-ray radiography, magnetic resonance (MR) imaging, computed tomography (CT), and positron emission tomography (PET), is routinely used for assessing tumor and anatomical tissue characteristics. In addition, radiology imaging can potentially provide valuable information for personalized medicine used to tailor treatment strategy based on the characteristics of individual patients and their tumors.

Typical cancers exhibit strong phenotypic differences that visibly manifest in radiology images. In the emerging field of radiomics, radiology images are analyzed by applying a large number of quantitative image features in order to objectively and quantitatively describe tumor phenotypes (see, for instance, Aerts H. J. W. L., "Decoding tumour phenotype by noninvasive imaging using a quantitative radiomics approach", Nature Communications, 5:4006, 2014).

While radiology images can provide information about a whole lesion and all lesions in the body of a patient, they have the disadvantage that the image features cannot be directly related to the biology of the disease due to a lack of spatial resolution and a lack of correlation of the measured signal with the biology of the tissue. For this reason, radiomics is based on correlating computed image features in a data-driven way, e.g., by correlating with therapy response. There is no ground truth information about the meaning of the features which correlate and results cannot be translated/extrapolated to other patient cohorts or cancers easily.

Pathology images, on the other hand, can provide sub-cellular resolution and—via immunostaining—direct information about the biology in the tumor. However, the images are limited to the location and size of the sample that was extracted from the patient. Using techniques such as advanced image analytics, machine learning and artificial intelligence, the rich features of pathology images can be interpreted in terms of cellular composition and tissue (sub)types which are of diagnostic relevance (see, for instance, Heindl A. et al., "Mapping spatial heterogeneity in the tumor microenvironment: a new era for digital pathology", Laboratory Investigation, Vol. 95, 2015, pages 377 to 384). Since (digital) pathology can analyze and describe cellular compositions and biomarker expression of tumor tissue, it is able to make knowledge-based links to therapy response. However, since pathology samples are in general not available from all lesions and only from biopsies which may not be representative for the whole tumor, the found correlations can be apparently much weaker than intrinsically possible.

It is therefore desirable to provide improved ways for an image-based characterization of cancers.

SUMMARY OF THE INVENTION

It is an object of the invention to provide a method for use in characterizing lesions in radiology images, which allows for an improved characterization of the lesions. It is a further object of the invention to provide a corresponding apparatus and computer program.

In a first aspect of the present invention, a method for use in characterizing lesions in radiology images is presented, comprising:
  performing a computer-based analysis of a pathology image of a sample of a lesion of a subject in order to recognize tissue and/or cellular characteristics of the lesion, wherein the analysis produces a derived pathology image that represents the recognized tissue and/or cellular characteristics,
  computing one or more radiology features for the lesion from a radiology image of the lesion,
  determining correlations between the computed one or more radiology features and the recognized tissue and/or cellular characteristics.

Previous work in radiomics has aimed at assessing the prognostic value of various quantitative image features derived from radiology images by correlating the computed image features in a data-driven way, e.g., by correlating with therapy response. However, the biological meaning of these features remains largely unknown with this approach and it becomes difficult to translate/extrapolate results to other patient cohorts or cancers (see, for instance, Parmar C., "Radiomic feature clusters and prognostic signatures specific for lung and head & neck cancer", Scientific reports, 5:11044, 2015). By performing a computer-based analysis of a pathology image of a sample of a lesion of a subject in order to recognize tissue and/or cellular characteristics of the lesion, wherein the analysis produces a derived pathology image that represents the recognized tissue and/or cellular characteristics, computing one or more radiology features for the lesion from a radiology image of the lesion, and determining correlations between the computed one or more radiology features and the recognized tissue and/or cellular characteristics, biological ground truth information can be used to identify radiology features that are indicative of certain tissue and/or cellular characteristics of a lesion and that may therefore be better suited for characterizing the lesion. Such radiology features can then be used together with the corresponding correlations for an improved characterization of lesions in radiology images.

The pathology image may be generated from a thin slice of the tissue of the lesion sample, which is obtained from a biopsy or resection of a lesion by fixation and paraffin embedding. Such a slice is typically placed on a glass slide and stained with hematoxylin and eosin (H&E) staining to increase contrast for visualizing the cellular and tissue morphology, allowing different cell types to be recognized based on morphological features like nuclear size and shape. Additionally, a specific staining, like immunohistochemistry (IHC) staining, immunofluorescence (IF) staining, or fluorescent in situ hybridization (FISH), can be applied in order to highlight e.g. the overexpression of proteins and genes in the tissue using antibodies and hybridization probes, respectively. The pathology image may then be acquired by digitally scanning the stained tissue slide. This allows for the computer-based analysis of the pathology image. Pathology images are typically acquired with a spatial resolution of about 0.25 micrometer, i.e., one square pixel of the digital image corresponds to a region of 0.25×0.25 micrometer of the sample placed on the glass slide.

The computer-based analysis of the pathology image preferably makes use of techniques such as advanced image analytics, machine learning and artificial intelligence, e.g., deep neural networks, in order to recognize the tissue and/or cellular characteristics of the lesion. Such analysis techniques are known in the art and can be found, for instance, in Heindl A. et al., "Mapping spatial heterogeneity in the tumor microenvironment: a new era for digital pathology", Laboratory Investigation, Vol. 95, 2015, pages 377 to 384. Since the computer-based analysis can highlight particular tissue and/or cellular characteristics independent of the appearance as a consequence of the particular staining procedure, a better correlation with the one or more radiology features computed from the radiology image of the lesion, in which different aspects of the lesion are accentuated, can be achieved.

The radiology image of the lesion may be acquired with various kinds of radiologic imaging modalities that are used in clinical practice, each with their own strengths and limitations. Examples include computed tomography (CT), magnetic resonance imaging (MRI), in particular, multiparametric MRI (mpMRI), positron emission tomography (PET), and single photon emission computed tomography (SPECT). Optionally, contrast agents can be used that enrich in a particular area of interest, e.g., a tumor, and allow visualization of the presence of certain molecules (molecular imaging) or metabolic processes (e.g., FDG) or tissue properties, like oxygenation or pH (MRI). A typical spatial resolution in CT or PET/CT is of the order of 4 millimeter. MRI resolution can go down to a millimeter depending on the location (brain is most controlled).

The one or more radiology features may comprise a vast number of different features, including different types, such as (i) intensity-based features, (ii) shape-based features, (iii) texture-based features, and (iv) wavelet-based features (see, for instance, Aerts H. J. W. L., "Decoding tumour phenotype by noninvasive imaging using a quantitative radiomics approach", Nature Communications, 5:4006, 2014). These features are typically implemented as image filters, wherein the mathematical definitions of the features can be found in the literature, for instance, in Haralick, R. M. et al., "Textural Features for Image Classification", IEEE Transactions on Systems, Man, and Cybernetics, Vol. 3, No. 6, 1973, pages 610 to 621, and Thibault, G., et al., "Advanced Statistical Matrices for Texture Characterization: Application to Cell Classification", IEEE Transactions on Biomedical Engineering, Vol. 61, No. 3, 2013, pages 630 to 637. A detailed description of texture features for radiomics can be found in Depeursinge, A. et al. (Eds.), "Biomedical Texture Analysis: Fundamentals, Tools and Challenges", Elsevier, 2017.

It is preferred that the method further comprises:
(i) characterizing the lesion in the radiology image based on at least a subset, such as one, two or more, of the one or more computed radiology features and the corresponding determined correlations, and/or
(ii) characterizing a different area of the same lesion in the same or a different radiology image of the same subject based on at least a subset, such as one, two or more, of the one or more radiology features computed for the different area of the same lesion and the corresponding determined correlations, and/or
(iii) characterizing a different lesion in a radiology image of the same or a different subject and/or the same lesion in a different radiology image of the subject based on at least a subset, such as one, two or more, of the one or more radiology features computed for the different lesion from the radiology image of the same or the different subject and/or for the same lesion from the different radiology image of the subject and the corresponding determined correlations. By doing so, the knowledge about how the one or more radiology features correlate with the recognized tissue and/or cellular characteristics can be used for the characterization of the lesion and/or of lesions for which biological ground truth information from pathology images is not available (including other parts of the same lesion). Preferably, this may also allow to generalize radiology features for particular cohorts of patients.

Preferably, in (i), (ii) and/or (iii) the subset of the one or more radiology features is selected based on the strength of the corresponding determined correlations. For instance, the subset may be selected to include only radiology features for which the correlation with the recognized tissue and/or cellular characteristics is found to be strong or significant, whereas radiology features with only weak or insignificant correlations may not be used in the characterization.

It is preferred that the spatial resolution of the derived pathology image substantially matches the spatial resolution of the radiology image(s). As mentioned above, radiology images are typically acquired with a spatial resolution of a few millimeters whereas pathology images have a much higher spatial resolution of 0.25 micrometer. This discrepancy in the spatial resolutions of the pathology image and of the radiology image of the lesion makes it difficult to directly compare the images. By making use of a derived pathology image that represents the recognized tissue and/or cellular characteristics at a spatial resolution that substantially matches the spatial resolution of the radiology image, the correlating step of correlating the computed one or more radiology features with the recognized tissue and/or cellular characteristics can be simplified.

Preferably, the method further comprises co-registering the radiology image of the lesion and the derived pathology image. Since it is the aim to identify radiology features that are indicative of certain tissue and/or cellular characteristics of a lesion, it is advantageous to determine spatial correspondence between the radiology image of the lesion and the derived pathology image. The particular recognized tissue and/or cellular characteristic in an area of the derived pathology image can then directly be used as biological ground truth for a corresponding area in the co-registered radiology image (see below).

Preferably, the co-registering step is based on an automatic feature recognition and/or employs spatial information determined by an image-guided biopsy of the sample. The former approach has the advantage that it does not rely on the availability of spatial information for the pathology image. However, it requires the presence of detectable features, such as feature points or other detectable structures, that are common in both the radiology image of the lesion and the derived pathology image. This may be used, for instance, with tissue obtained from a tumor resection, since in this case sufficient tissue material with recognizable characteristics will typically be available. The latter approach, on the other hand, can employ spatial information determined by an image-guided biopsy of the sample. If such information is available, it may help in making the co-registration more robust. For example, if the radiology image is a tomographic image representing a three-dimensional (3D) reconstruction of the subject or part of the subject, two-dimensional (2D) slices of the tomographic image can be selected in different directions. If information about the location and orientation of the biopsy of the sample within the subject is available, this information can be used to robustly select the part and orientation of the radiology image that matches the derived pathology image (as well as the pathology image underlying the derived pathology image).

It is preferred that the determining step comprises selecting at least one area in the derived pathology image representing a particular recognized tissue and/or cellular characteristic and analyzing the computed one or more radiology features for a corresponding area in the co-registered radiology image.

This may be specifically applicable where the pathology image is based on tissue that is obtained from a tumor resection. For instance, if it is found that a particular computed radiology feature generally provides a strong response in areas of the co-registered radiology image that correspond to areas of the derived pathology image representing a particular recognized tissue and/or cellular characteristic, the particular computed radiology feature may be considered as having a strong correlation with the particular recognized tissue and/or cellular characteristic. In contrast, if the response of a particular computed radiology feature differs largely in areas of the co-registered radiology image that correspond to areas of the derived pathology image representing a particular recognized tissue and/or cellular characteristic, the particular computed radiology feature may be considered as having only a weak—or even no— correlation with the particular recognized tissue and/or cellular characteristic.

By doing so, it can be assessed whether the computed one or more radiology features are indeed indicative for the particular recognized tissue and/or cellular characteristic of the selected at least one area in the derived pathology image.

It is also preferred that the determining step comprises computing one or more features for the at least one area from the derived pathology image and correlating the one or more features computed for the at least one area from the derived pathology image and the computed one or more radiology features for the corresponding area in the co-registered radiology image. By doing so, the derived pathology image and the radiology image can be analyzed for similarities and/or a similar features and in this way features in the derived pathology image can be identified that show correspondence to radiology features in the radiology image. Such features may be, for example, image filter based features and they may be the same as the radiology features that are used for the analysis of the radiology image. For instance, one may calculate the entropy of the fat distribution, or the Gaussian of stromal tissue, in the derived pathology image and determine whether there is a correlation with a corresponding filter in the radiology image. In this context, it is possible to adjust the resolution and/or the contrast of the derived pathology image. This provides the freedom, based on a particular biological reasoning, to select the resolution and/or the contrast of the derived radiology image and to see which filter-based parameters respond and correspond to the output of the radiology features. In other words, this provides two degrees of freedom: (1) the biology (which computer-based analysis (detectors) is run on the raw pathology image), and (2) the resolution and contrast (morphological parameters), which can be adjusted in order to analyze the derived pathology image in a similar way as the radiology image, i.e., for instance, filter-based.

Alternatively, it is preferred that the determining step comprises computing one or more features that are characteristic for the whole sample of the lesion from the derived pathology image and correlating the computed one or more radiology features and the one or more features computed from the derived pathology image, wherein the correlating does not depend on a co-registering of the radiology image of the lesion and the derived pathology image. This may be specifically applicable where the pathology image is based on tissue that is obtained from a biopsy of the sample, since in this case only a small amount of tissue material may be available, which may not be analyzed for different areas but of which the biology may be represented, for instance, by average values that may be correlated with radiology features computed from the radiology image for a region of the lesion from which the biopsy was taken. Since no different areas of the lesion are correlated separately in this approach, there is no real co-registration required, but the only concern is that the correlation is determined between corresponding parts of the lesion.

It is preferred that the recognized tissue and/or cellular characteristics comprise at least one of: (i) one or more tissue types, (ii) distributions of one or more cell types, and (iii) calcifications. These tissue and/or cellular characteristics provide important information about the biology of a lesion that can be used to advantage in the diagnosis, response prediction and monitoring of cancer. For instance, the computer-based analysis of the pathology image may produce a derived pathology image in which (tumor) epithelial tissue is distinguished from stromal connective tissue, fat tissue and background. Or the derived pathology image only distinguishes epithelial tissue from non-epithelial tissue. An alternative type of analysis of the pathology image would be to detect particular cell types, like tumor cells or immune cells, and then represent density distributions of the particular cell type in the derived pathology image. Also, the distribution may be represented for all cells not distinguishing the cell type. A further alternative analysis of the pathology image would be to detect pieces of calcifications and to represent them in the derived pathology image.

The staining and computer-based analysis of the pathology image can preferably be selected and tuned depending on the radiologic imaging modality. For instance, morphological features in MRI may be correlated with tissue type distributions derived from H&E-stained tissue images, while FDG-PET metabolic activity may correlate with cellular densities derived from H&E-stained tissue images, and immune-PET images might directly be correlated with densities of cells stained in immunohistochemistry (IHC) with an antibody targeting the same cell type as the immune-PET contrast agent.

It is preferred that the characterizing step is performed without having a pathology image available for the different lesion. Thus, biological ground truth information from pathology images does not have to be available for all lesions. Instead, it suffices that the correlations of the computed one or more radiology features with the recognized tissue and/or cellular characteristics have been determined in order to characterize a different lesion without the need for individual pathology information based on the correlations.

It is further preferred that the different radiology image of the subject is acquired at a different point in time for which no pathology image is available for the lesion. This allows for a repeated characterization of the lesion over time, e.g., for tracking progression of the disease or treatment response, without having to provide a current sample of the lesion for each new characterization.

It is further preferred that the characterizing step comprises characterizing multiple lesions in one or more radiology images of the subject based on at least the subset of the one or more radiology features and the corresponding correlations and determining a characteristic of a cancer of the subject based on the multiple lesion characterization. Many cancers are known to exhibit substantial inter-lesion heterogeneities, which poses significant challenges in designing effective treatment strategies. Such cancers may not be sufficiently characterized based on the characterization of a single lesion alone. By performing a multiple lesion characterization based on at least the subset of the one or more radiology features and the corresponding correlations, a more accurate picture of the characteristic of the cancer, for instance, of the heterogeneity of the cancer may be obtained. This may allow for the creation of more refined treatment strategies that incorporate knowledge of heterogeneity to yield higher efficacy.

In a further aspect of the present invention, a method for characterizing lesions in radiology images is presented, comprising:
  computing one or more radiology features for the lesion from a radiology image of the lesion,
  characterizing the lesion in the radiology image based on at least the one or more computed radiology features and corresponding correlations,
  wherein the one or more radiology features and the corresponding correlations have been selected as a subset one or more radiology features that had been computed as defined in any of claims 1 to 12 for one or more different lesions of one or more different subjects and the corresponding determined correlations.

This aspect foresees that radiology features and the corresponding determined correlations may be pre-determined from a subject or from a suitable cohort of subjects using the method as defined in any of claims 1 to 12. These radiology features, e.g., the ones that showed signification correlations to the biological information from the pathology, may then be generalized in order to extract information about the biology from radiology images of other subjects.

In a further aspect of the present invention, an apparatus for use in characterizing lesions in radiology images is presented, comprising:
  an analyzing unit for performing a computer-based analysis of a pathology image of a sample of a lesion of a subject in order to recognize tissue and/or cellular characteristics of the lesion, wherein the analysis produces a derived pathology image that represents the recognized tissue and/or cellular characteristics,
  a computing unit for computing one or more radiology features for the lesion from a radiology image of the lesion,
  a determining unit for determining correlations between the computed one or more radiology features and the recognized tissue and/or cellular characteristics.

In a further aspect of the present invention, a computer program for use in characterizing lesions in radiology images is presented, the computer program comprising program code means for causing an apparatus as defined in claim 14 to carry out the steps of the method as defined in any of claims 1 to 12, when the computer program is run on a computer controlling the apparatus.

It shall be understood that the method of claim 1, the apparatus of claim 14, and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
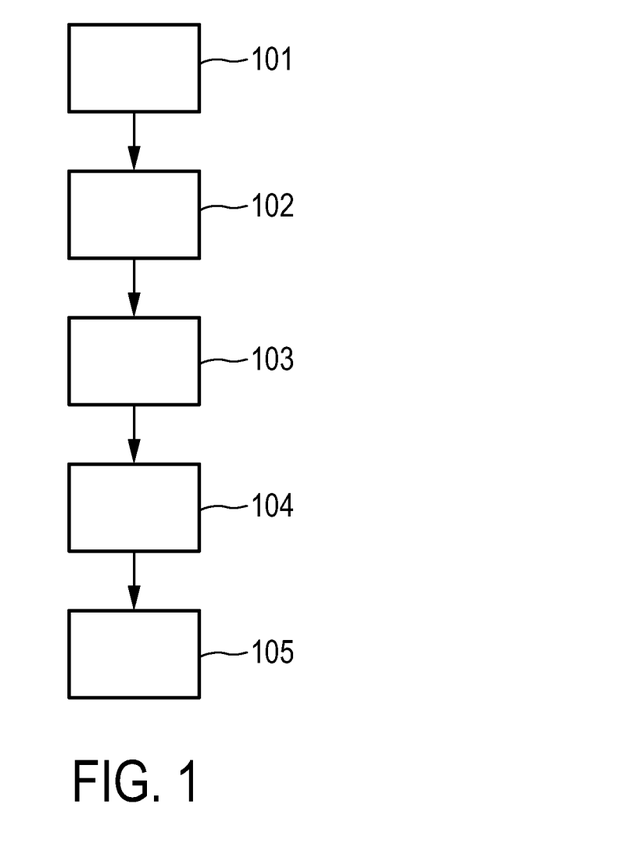
FIG. 1 illustrates a flowchart of an embodiment of a method for use in characterizing lesions in radiology images.

FIG. 1 illustrates a flowchart of an embodiment of a method for use in characterizing lesions in radiology images. The method assumes that a pathology image of a sample of a lesion of a subject as well as a radiology image of the lesion have been acquired in preceding steps. Alternatively, the steps of acquiring these images may also be part of the method itself.

The pathology image may be generated as described above using a known staining, such as H&E staining, IHC staining, IF staining, or FISH. The radiology image of the lesion may be acquired using a radiologic imaging modality such as CT, MRI, in particular, mpMRI, PET, or SPECT. Optionally, contrast agents can be used that enrich in a particular area of interest, e.g., a tumor, and allow visualization of the presence of certain molecules (molecular imaging) or metabolic processes (e.g., FDG) or tissue properties, like oxygenation or pH (MRI).

In step 101, a computer-based analysis of the pathology image of the sample of the lesion of the subject is performed in order to recognize tissue and/or cellular characteristics of the lesion, wherein the analysis produces a derived pathology image that represents the recognized tissue and/or cellular characteristics. The contrast and resolution of the derived image can be varied to analyze and/or optimize the sensitivity of the correlation with the radiology image. Multiple detectors for different biological characteristics can be combined to generate the derived pathology image.

The recognized tissue and/or cellular characteristics comprise at least one of: (i) one or more tissue types, (ii) distributions of one or more cell types, and (iii) calcifications. These tissue and/or cellular characteristics provide important information about the biology of a lesion that can be used to advantage in the diagnosis, response prediction and monitoring of cancer.

The computer-based analysis of the pathology image preferably makes use of techniques such as advanced image analytics, machine learning and artificial intelligence, e.g., deep neural networks, in order to recognize the tissue and/or cellular characteristics of the lesion. Such analysis techniques are known in the art and can be found, for instance, in Heindl A. et al., "Mapping spatial heterogeneity in the tumor microenvironment: a new era for digital pathology", Laboratory Investigation, Vol. 95, 2015, pages 377 to 384. Since the computer-based analysis can highlight particular tissue and/or cellular characteristics independent of the appearance as a consequence of the particular staining procedure, a better correlation with the one or more radiology features computed from the radiology image of the lesion, in which different aspects of the lesion are accentuated, can be achieved.

Figure 2:
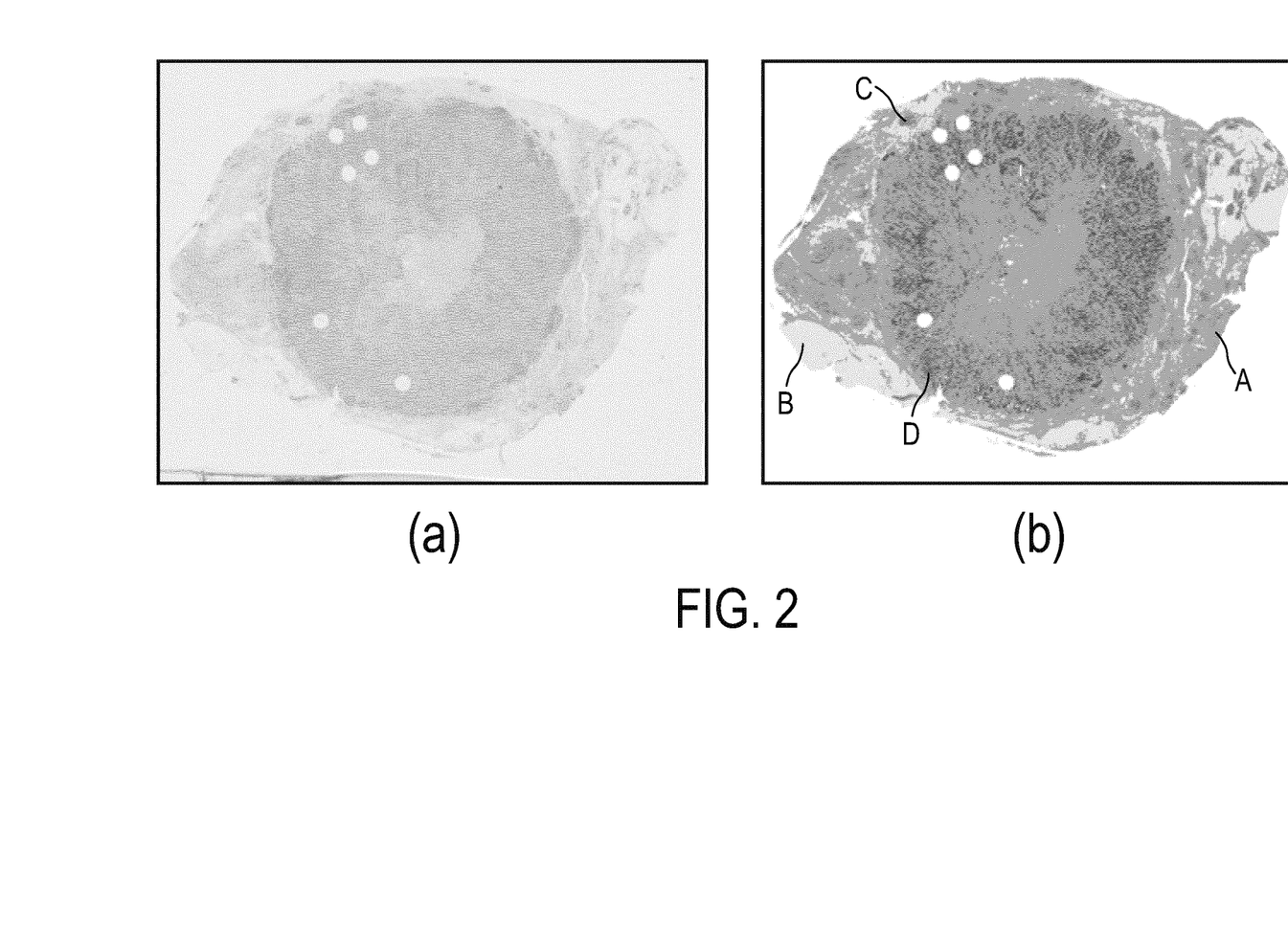
FIG. 2 shows schematically and exemplarily a pathology image and a derived pathology image representing recognized tissue characteristics.

To give an example, FIG. 2 shows schematically and exemplarily a pathology image and a derived pathology image representing recognized tissue characteristics. In this case, a sample of a lesion of a subject has been obtained by resection of a breast tumor and the slice has been stained using H&E staining (see FIG. 2(a)). A computer-based analysis has then been performed on the pathology image in order to recognize tissue characteristics of the lesion (see FIG. 2(b)). Here, different types of tissue were represented in a false color representation—shown only in gray level in the figure. For instance, the areas indicated by 'A', 'B', 'C' and 'D' correspond to different types of tissue, namely, tumor epithelial tissue ('D'), stromal connective tissue ('A'), fat tissue ('B'), and acini ('C'). As can be seen from FIG. 2, the different types of tissue are clearly distinguished in the derived pathology image, which makes it easier to determine the correlations with the one or more computed radiology features.

In an alternative example that is not shown in the figures, the derived pathology image may only distinguish epithelial tissue from non-epithelial tissue. Moreover, an alternative type of analysis of the pathology image would be to detect particular cell types, like tumor cells or immune cells, and then represent density distributions of the particular cell type in the derived pathology image. Also, the distribution may be represented for all cells not distinguishing the cell type. A further alternative analysis of the pathology image would be to detect pieces of calcifications and to represent them in the derived pathology image.

With returning reference to FIG. 1, in step 102, the radiology image of the lesion and the derived pathology image are co-registered.

Since it is the aim to identify radiology features that are indicative of certain tissue and/or cellular characteristics of a lesion, it is advantageous to determine spatial correspondence between the radiology image of the lesion and the derived pathology image. The particular recognized tissue and/or cellular characteristic in an area of the derived pathology image can then directly be used as biological ground truth for a corresponding area in the co-registered radiology image (see below). The co-registering step may be based on an automatic feature recognition and/or it may employ spatial information determined by an image-guided biopsy of the sample.

In step 103, one or more radiology features are computed for the lesion from a radiology image of the lesion.

As mentioned above, the one or more radiology features may comprise a vast number of different features, including different types, such as (i) intensity-based features, (ii) shape-based features, (iii) texture-based features, and (iv) wavelet-based features.

In step 104, correlations between the computed one or more radiology features and the recognized tissue and/or cellular characteristics are determined.

In this embodiment, at least one area in the derived pathology image representing a particular recognized tissue and/or cellular characteristic is selected and the computed one or more radiology features are analyzed for a corresponding area in the co-registered radiology image.

For instance, if it is found that a particular computed radiology feature generally provides a strong response in areas of the co-registered radiology image that correspond to areas of the derived pathology image representing a particular recognized tissue and/or cellular characteristic, the particular computed radiology feature may be considered as having a strong correlation with the particular recognized tissue and/or cellular characteristic. In contrast, if the response of a particular computed radiology feature differs largely in areas of the co-registered radiology image that correspond to areas of the derived pathology image representing a particular recognized tissue and/or cellular characteristic, the particular computed radiology feature may be considered as having only a weak—or even no—correlation with the particular recognized tissue and/or cellular characteristic.

By means of the method as outlined so far, biological ground truth information can be used to identify radiology features that are indicative of certain tissue and/or cellular characteristics of a lesion and that may therefore be better suited for characterizing the lesion. Such radiology features can then be used together with the corresponding correlations for an improved characterization of lesions in radiology images.

In optional step 105, (i) the lesion in the radiology image is characterized based on at least a subset of the one or more computed radiology features and the corresponding determined correlations, and/or (ii) a different area of the same lesion in the same or a different radiology image of the same subject is characterized based on at least a subset of the one or more radiology features computed for the different area of the same lesion and the corresponding determined correlations, and/or (iii) a different lesion in a radiology image of the same or a different subject and/or the same lesion in a different radiology image of the subject is characterized based on at least a subset of the one or more radiology features computed for the different lesion from the radiology image of the same or the different subject and/or for the same lesion from the different radiology image of the subject and the corresponding correlations.

By doing so, the knowledge about how the one or more radiology features correlate with the recognized tissue and/or cellular characteristics can be used for the characterization of the lesion and/or of lesions for which biological ground truth information from pathology images is not available. Preferably, this may also allow to generalize radiology features for particular cohorts of patients.

In this embodiment, the subset of the one or more radiology features is selected based on the strength of the corresponding determined correlations. In particular, the subset is selected to include only radiology features for which the correlation with the recognized tissue and/or cellular characteristics is found to be strong or significant, whereas radiology features with only weak or insignificant correlations are not used in the characterization.

It shall be noted that the characterizing step is preferably performed without having a pathology image available for the different lesion. Thus, biological ground truth information from pathology images does not have to be available for all lesions. Instead, it suffices that the correlations of the computed one or more radiology features with the recognized tissue and/or cellular characteristics have been determined in order to characterize a different lesion without the need for individual pathology information based on the correlations.

Likewise, it is preferred that the different radiology image of the subject is acquired at a different point in time for which no pathology image is available for the lesion.

In this embodiment, the characterizing step comprises characterizing multiple lesions in one or more radiology images of the subject based on at least the subset of the one or more radiology features and the corresponding correlations and determining a characteristic of a cancer of the subject based on the multiple lesion characterization. By doing so, a more accurate picture of the characteristic of the cancer, for instance, of the heterogeneity of the cancer may be obtained. This may allow for the creation of more refined treatment strategies that incorporate knowledge of heterogeneity to yield higher efficacy.

The above-outlined method for use in characterizing lesions in radiology images may be considered as being a 'location-based' method, since it includes the step 102 of co-registering the radiology image of the lesion and the derived pathology image and since it makes use of the location information in the step 104 of determining the correlations between the computed one or more radiology features and the recognized tissue and/or cellular characteristics.

In a variant of the 'co-location based' method, the determining step comprises computing one or more features for the at least one area from the derived pathology image and correlating the one or more features computed for the at least one area from the derived pathology image and the computed one or more radiology features for the corresponding area in the co-registered radiology image from the derived pathology image. By doing so, the derived pathology image and the radiology image can be analyzed for similarities and/or a similar features and in this way features in the derived pathology image can be identified that show correspondence to radiology features in the radiology image. Such features may be, for example, image filter based features and they may be the same as the radiology features that are used for the analysis of the radiology image (see Aerts H. J. W. L., "Decoding tumour phenotype by noninvasive imaging using a quantitative radiomics approach", Nature Communications, 5:4006, 2014). For instance, one may calculate the entropy of the fat distribution, or the Gaussian of stromal tissue, in the derived pathology image and determine whether there is a correlation with a corresponding filter in the radiology image. In this context, it is possible to adjust the resolution and/or the contrast of the derived radiology image. This provides the freedom, based on a particular biological reasoning, to select the resolution and/or the contrast of the derived radiology image and to see which filter-based parameters respond and correspond to the output of the radiology features. In other words, this provides two degrees of freedom: (1) the biology (which computer-based analysis (detectors) is run on the raw pathology image), and (2) the resolution and contrast (morphological parameters), which can be adjusted in order to analyze the derived pathology image in a similar way as the radiology image, i.e., for instance, filter-based. This may still be regarded as being a 'co-location based' approach.

In another embodiment of a method for use in characterizing lesions in radiology images, the correlations may be determined using a purely 'feature based' approach, i.e., the step 102 of co-registering the radiology image of the lesion and the derived pathology image can be omitted. In particular, the determining step comprises computing one or more features that are characteristic for the whole sample of the lesion from the derived pathology image and correlating the computed one or more radiology features and the one or more features computed from the derived pathology image, wherein the correlating does not depend on a co-registering of the radiology image of the lesion and the derived pathology image. As mentioned above, this may be specifically applicable where the pathology image is based on tissue that is obtained from a biopsy of the sample, since in this case only a small amount of tissue material may be available, which may not be analyzed for different areas but of which the biology may be represented, for instance, by average values that may be correlated with radiology features computed from the radiology image for a region of the lesion from which the biopsy was taken. Since no different areas of the lesion are correlated separately in this approach, there is no real co-registration required, but the only concern is that the correlation is determined between corresponding parts of the lesion. The one or more features computed from the derived pathology image may be a subset of those that are also used in radiomics, such as explained in Aerts H. J. W. L., "Decoding tumour phenotype by noninvasive imaging using a quantitative radiomics approach", Nature Communications, 5:4006, 2014

Both in the variant of the 'co-location based' method and in the 'feature based' approach, it may be necessary to create gray level images from the derived pathology images.

Figure 3:
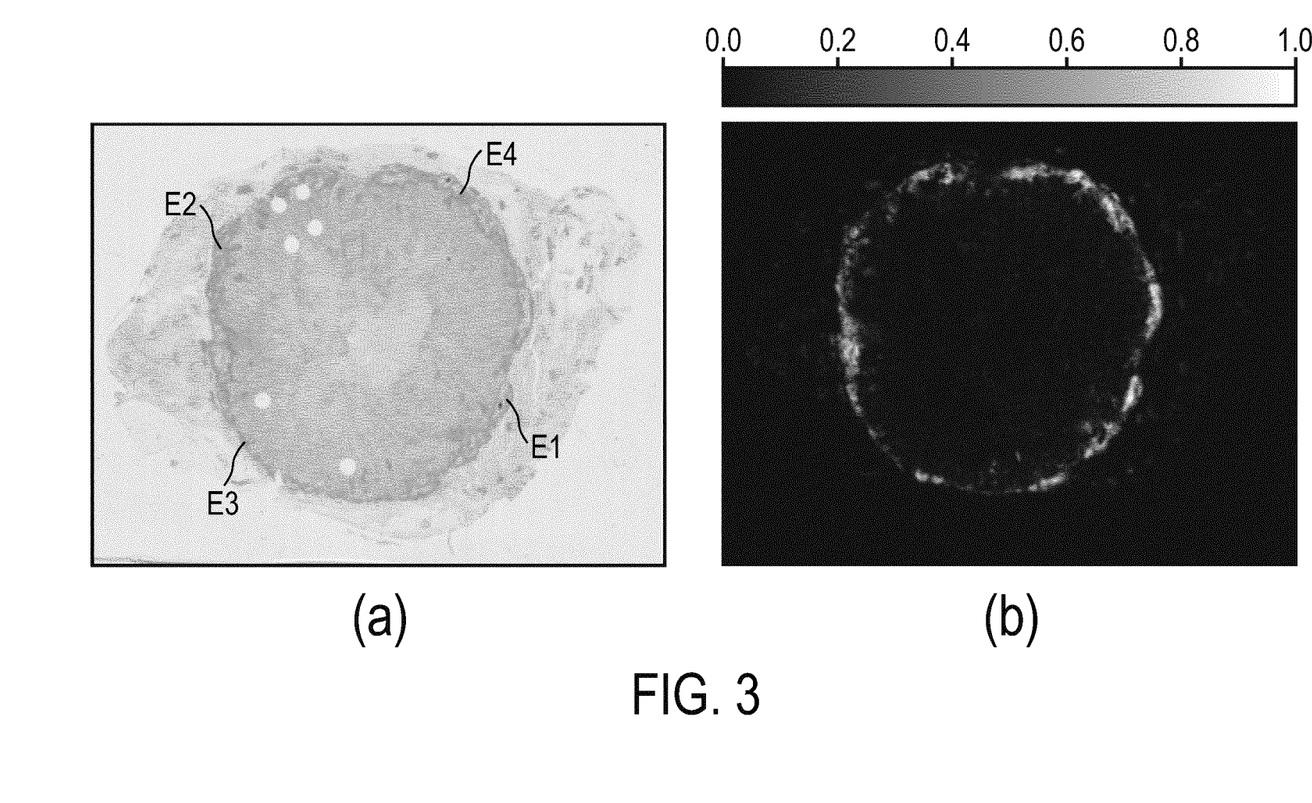
FIG. 3 shows schematically and exemplarily a derived pathology image and a conversion into a gray level image.

To give an example, FIG. 3 shows schematically and exemplarily a derived pathology image and a conversion into a gray level image. In this case, a sample of a lesion of a subject has been obtained by resection of a breast tumor and a computer-based analysis of the pathology image of the H&E stained slice has been performed in order to determine a density map of lymphocytes. This density map has been overlaid on the pathology image in order to produce the derived pathology image (see FIG. 3(a)). Here, the different densities of the lymphocytes were represented in a false color representation—shown only in gray level in the figure. For instance, the areas indicated by 'E1', 'E2', 'E3' and 'E4' correspond to areas with an accumulation of lymphocytes, which tend to be located around the lesion. The result of a conversion of the derived pathology image into a gray level image is then shown in FIG. 3(b). This representation can be generated in a straightforward manner by assigning gray values to the binned scaled density range.

Figure 4:
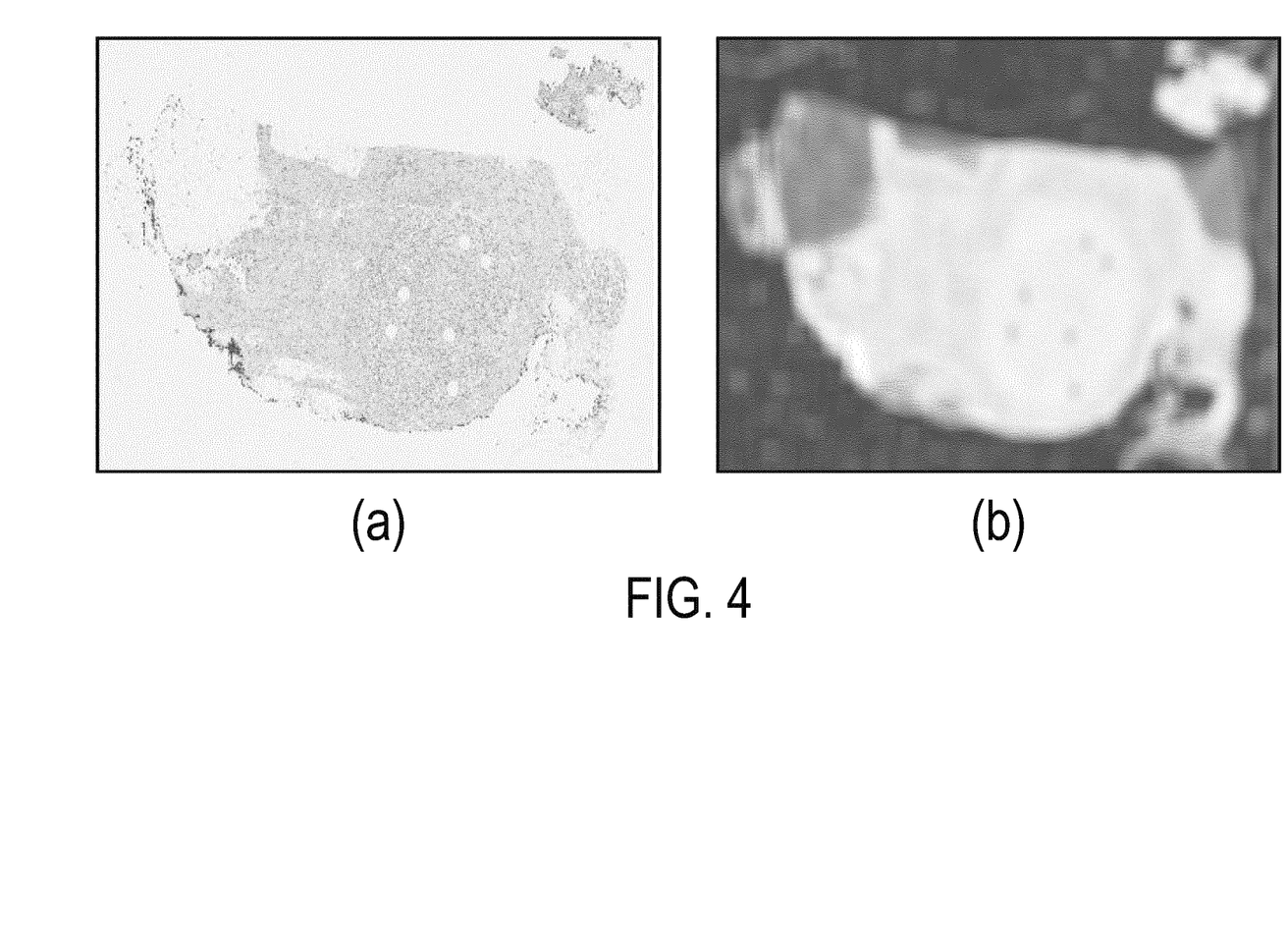
FIG. 4 shows schematically and exemplarily a conversion of different tissue type classifications of a derived pathology image into an entropy map.

FIG. 4 shows schematically and exemplarily a conversion of different tissue type classifications of a derived pathology image into an entropy map. In this case, FIG. 4(a) shows an raw H&E stained pathology image, FIG. 4(c) shows a derived pathology image representing different types of tissue, namely, tumor epithelial tissue, stromal connective tissue, fat tissue, and background, and FIG. 4(e) shows a derived pathology image representing different types of tissue, epithelial tissue vs. non-epithelial tissue—each represented as a gray level image. FIGS. 4(b), (d), and (f) then show the conversion into an entropy map, respectively. As can be seen from the figure, the entropy maps of the derived pathology images are much more rich and informative than the entropy map of the raw H&E stained pathology image.

The computer-based analysis used on the pathology images can highlight particular features independent of the appearance as a consequence of a particular staining procedure and in this way better correlate with the features derived from radiology which accentuate very different features. The computer-based analysis used for the pathology image can be selected and tuned depending on the radiology modality. By analyzing the strongest correlating features in between the derived pathology image and the radiology image those features can be prioritized and preferentially used in the analysis and interpretation of radiology images from other lesions in order to arrive at a conclusion for the patient with respect to characteristics of the cancer, for instance, related to the heterogeneity.

Figure 5:
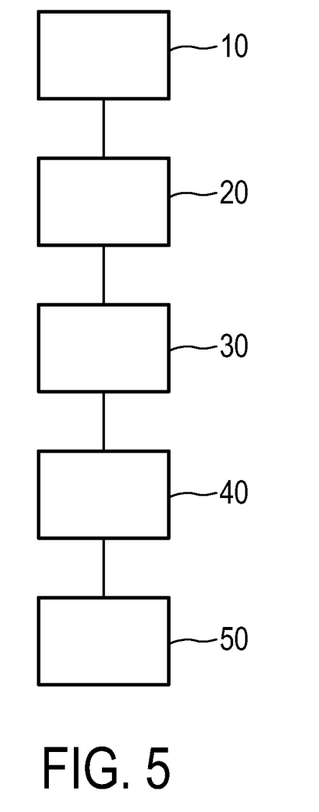
FIG. 5 shows schematically and exemplarily an embodiment of an apparatus for use in characterizing lesions in radiology images.

FIG. 5 shows schematically and exemplarily an embodiment of an apparatus for use in characterizing lesions in radiology images. The apparatus can be configured to perform the method for use in characterizing lesions in radiology images as outlined above.

In this embodiment, the apparatus comprises an analyzing unit 10 for performing a computer-based analysis of a pathology image of a sample of a lesion of a subject in order to recognize tissue and/or cellular characteristics of the lesion, wherein the analysis produces a derived pathology image that represents the recognized tissue and/or cellular characteristics. The apparatus further comprises a co-registration unit 20 for co-registering the radiology image of the lesion and the derived pathology image. Furthermore, the apparatus comprises a computing unit 30 for computing one or more radiology features for the lesion from a radiology image of the lesion, and a determining unit 40 for determining correlations between the computed one or more radiology features and the recognized tissue and/or cellular characteristics. Yet further, the apparatus optionally comprises a characterization unit 50 for (i) characterizing the lesion in the radiology image based on at least a subset of the one or more computed radiology features and the corresponding determined correlations, and/or (ii) characterizing a different area of the same lesion in the same or a different radiology image of the same subject based on at least a subset of the one or more radiology features computed for the different area of the same lesion and the corresponding determined correlations, and/or (iii) characterizing a different lesion in a radiology image of the same or a different subject and/or the same lesion in a different radiology image of the subject based on at least a subset of the one or more radiology features computed for the different lesion from the radiology image of the same or the different subject and/or for the same lesion from the different radiology image of the subject and the corresponding determined correlations.

Other variations to the disclosed realizations can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

One or more steps of the method illustrated in FIG. 1 may be implemented in a computer program product that may be executed on a computer. The computer program product may comprise a non-transitory computer-readable recording medium on which a control program is recorded (stored), such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other non-transitory medium from which a computer can read and use.

Alternatively, the one or more steps of the method may be implemented in transitory media, such as a transmittable carrier wave in which the control program is embodied as a data signal using transmission media, such as acoustic or light waves, such as those generated during radio wave and infrared data communications, and the like.

The exemplary method may be implemented on one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like. In general, any device, capable of implementing a finite state machine that is in turn capable of implementing the flowchart shown in FIG. 1, can be used to implement one or more steps of the method for use in characterizing lesions in radiology images as illustrated. As will be appreciated, while the steps of the method may all be computer implemented, in some embodiments one or more of the steps may be at least partially performed manually.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Any reference signs in the claims should not be construed as limiting the scope.

The invention relates to a method for use in characterizing lesions in radiology images, comprising performing a computer-based analysis of a pathology image of a sample of a lesion of a subject in order to recognize tissue and/or cellular characteristics of the lesion, wherein the analysis produces a derived pathology image that represents the recognized tissue and/or cellular characteristics, computing one or more radiology features for the lesion from a radiology image of the lesion, and determining correlations between the computed one or more radiology features and the recognized tissue and/or cellular characteristics. With this method, biological ground truth information can be used to identify radiology features that are indicative of certain tissue and/or cellular characteristics of a lesion and that may therefore be better suited for characterizing the lesion. Such radiology features can then be used together with the corresponding correlations for an improved characterization of lesions in radiology images.

Features of some arrangements are set out in the following numbered paragraphs:

1. A method for use in characterizing lesions in radiology images, comprising:
    performing (101) a computer-based analysis of a pathology image of a sample of a lesion of a subject in order to recognize tissue and/or cellular characteristics of the lesion, wherein the analysis produces a derived pathology image that represents the recognized tissue and/or cellular characteristics,
    computing (103) one or more radiology features for the lesion from a radiology image of the lesion, and
    determining (104) correlations between the computed one or more radiology features and the recognized tissue and/or cellular characteristics.

2. The method as defined in paragraph 1, wherein the method further comprises:
   (i) characterizing the lesion in the radiology image based on at least a subset of the one or more computed radiology features and the corresponding determined correlations, and/or
   (ii) characterizing a different area of the same lesion in the same or a different radiology image of the same subject based on at least a subset of the one or more radiology features computed for the different area of the same lesion and the corresponding determined correlations, and/or
   (iii) characterizing a different lesion in a radiology image of the same or a different subject and/or the same lesion in a different radiology image of the subject based on at least a subset of the one or more radiology features computed for the different lesion from the radiology image of the same or the different subject and/or for the same lesion from the different radiology image of the subject and the corresponding determined correlations.

3. The method as defined in paragraph 2, wherein in (i), (ii) and/or (iii) the subset of the one or more radiology features is selected based on the strength of the corresponding determined correlations.

4. The method as defined in any of paragraphs 1 to 3, wherein the spatial resolution of the derived pathology image substantially matches the spatial resolution of the radiology image(s).

5. The method as defined in any of paragraphs 1 to 4, wherein the method further comprises co-registering the radiology image of the lesion and the derived pathology image.

6. The method as defined in paragraph 5, wherein the co-registering step is based on an automatic feature recognition and/or employs spatial information determined by an image-guided biopsy of the sample.

7. The method as defined in paragraph 5 or 6, wherein the determining step comprises selecting at least one area in the derived pathology image representing a particular recognized tissue and/or cellular characteristic and analyzing the computed one or more radiology features for a corresponding area in the co-registered radiology image.

8. The method as defined in paragraph 1, wherein the determining step comprises computing one or more features for the at least one area from the derived pathology image and correlating the one or more features computed for the at least one area from the derived pathology image and the computed one or more radiology features for the corresponding area in the co-registered radiology image.

9. The method as defined in any of paragraphs 1 to 4, wherein the determining step comprises computing one or more features that are characteristic for the whole sample of the lesion from the derived pathology image and correlating the computed one or more radiology features and the one or more features computed from the derived pathology image, wherein the correlating does not depend on a co-registering of the radiology image of the lesion and the derived pathology image.

10. The method as defined in any of paragraphs 1 to 9, wherein the recognized tissue and/or cellular characteristics comprise at least one of: (i) one or more tissue types, (ii) distributions of one or more cell types, and (iii) calcifications.

11. The method as defined in any of paragraphs 2 to 10, wherein the characterizing step is performed without having a pathology image available for the different lesion, and/or wherein the different radiology image of the subject is acquired at a different point in time for which no pathology image is available for the lesion.

12. The method as defined in any of paragraphs 2 to 11, wherein the characterizing step comprises characterizing multiple lesions in one or more radiology images of the subject based on at least the subset of the one or more radiology features and the corresponding correlations and determining a characteristic of a cancer of the subject based on the multiple lesion characterization.

13. A method for characterizing lesions in radiology images, comprising:
   computing one or more radiology features for the lesion from a radiology image of the lesion,
   characterizing the lesion in the radiology image based on at least the one or more computed radiology features and corresponding correlations,
   wherein the one or more radiology features and the corresponding correlations have been selected as a subset of one or more radiology features that had been computed as defined in any of paragraphs 1 to 12 for one or more different lesions of one or more different subjects and the corresponding determined correlations.

14. An apparatus for use in characterizing lesions in radiology images, comprising:
   an analyzing unit (10) for performing a computer-based analysis of a pathology image of a sample of a lesion of a subject in order to recognize tissue and/or cellular characteristics of the lesion, wherein the analysis produces a derived pathology image that represents the recognized tissue and/or cellular characteristics,
   a computing unit (30) for computing one or more radiology features for the lesion from a radiology image of the lesion, and
   a determining unit (40) for determining correlations between the computed one or more radiology features and the recognized tissue and/or cellular characteristics.

15. A computer program for use in characterizing lesions in radiology images, the computer program comprising program code means for causing an apparatus as defined in paragraph 14 to carry out the steps of the method as defined in any of paragraphs 1 to 12, when the computer program is run on a computer controlling the apparatus.

The invention claimed is:
1. A method for characterizing lesions in radiology images, comprising:
   performing a computer-based analysis comprising one or more of: advanced image analytics, machine learning, or artificial intelligence of a pathology image of a sample of a lesion of a subject in order to recognize tissue or cellular characteristics of the lesion, wherein the analysis produces a derived pathology image representative of the recognized tissue or cellular characteristics,
   co-registering a radiology image of the lesion and the derived pathology image;
   computing one or more radiology features for the radiology image of the lesion;
   determining correlations between the computed one or more radiology features and recognized tissue or cellular characteristics in the derived pathology image, by computing one or more features that are characteristic for a whole sample of the lesion from the derived pathology image and correlating the computed one or more radiology features and one or more features computed from the derived pathology image, wherein the correlating does not depend on co-registering the radiology image of the lesion and the derived pathology image; and characterizing the lesion in the radiology image based on at least a subset of the one or more computed radiology features and the corresponding determined correlations.

2. The method as of claim 1, wherein the method further comprises one or more of:
  (i) characterizing an area of the lesion in a same or different radiology image associated with the same subject based on at least a subset of the one or more computed radiology features for the area of the lesion and the determined correlations between the computed one or more radiology features and recognized tissue or cellular characteristics in the derived pathology image, or
  (ii) characterizing a different lesion in a radiology image associated with the same or a different subject or the same lesion in a different radiology image associated with the subject based on at least a subset of the one or more radiology features computed for the different lesion from the radiology image of the same or the different subject and/or for the same lesion from the different radiology image of the subject and the corresponding determined correlations between the computed one or more radiology features and recognized tissue and/or cellular characteristics in the derived pathology image.

3. The method as of claim 2, wherein the subset of the one or more radiology features is selected based on the strength of the corresponding determined correlations.

4. The method of claim 2, wherein the characterizing step is performed without having a pathology image available for the different lesion, and wherein the different radiology image of the subject is acquired at a different point in time for which no pathology image is available for the lesion.

5. The method of claim 2, wherein the characterizing step comprises: characterizing multiple lesions in one or more radiology images of the subject based on at least the subset of the one or more radiology features and the corresponding correlations and determining a characteristic of a cancer of the subject based on the multiple lesion characterization.

6. The method of claim 1, wherein the spatial resolution of the derived pathology image is adjusted to substantially match the spatial resolution of the radiology image(s).

7. The method of claim 1, wherein the co-registering step is based on an automatic feature recognition or employs spatial information determined by an image-guided biopsy of the sample.

8. The method of claim 1, wherein the determining step comprises: selecting at least one area in the derived pathology image representing a particular recognized tissue or cellular characteristic and analyzing the computed one or more radiology features for a corresponding area in the co-registered radiology image.

9. The method of claim 1, wherein the determining step comprises: computing one or more features for at least one area from the derived pathology image and correlating the one or more features computed for the at least one area from the derived pathology image and the computed one or more radiology features for a corresponding area in the co-registered radiology image.

10. The method of claim 1, wherein the recognized tissue or cellular characteristics comprise at least one of: (i) one or more tissue types, (ii) distributions of one or more cell types, and (iii) calcifications.

11. An apparatus for use in characterizing lesions in radiology images, comprising:
  an analyzing unit for performing a computer-based analysis comprising one or more of: advanced image analytics, machine learning, or artificial intelligence of a pathology image of a sample of a lesion of a subject in order to recognize tissue or cellular characteristics of the lesion, wherein the analysis produces a derived pathology image that representative of the recognized tissue or cellular characteristics;
  a co-registering unit for co-registering a radiology image of the lesion and the derived pathology image;
  a computing unit for computing one or more radiology features for the radiology image of the lesion;
  a determining unit for determining correlations between the computed one or more radiology features and recognized tissue or cellular characteristics in the derived pathology image, wherein the correlations are based on one or more computed features that are characteristic for a whole sample of the lesion from the derived pathology image and the determining unit correlates the computed one or more radiology features and one or more features computed from the derived pathology image, wherein the correlating does not depend on co-registering the radiology image of the lesion and the derived pathology image; and
  a characterization unit for characterizing the lesion in the radiology image based on at least a subset of the one or more computed radiology features and the corresponding determined correlations.

12. A non-transitory computer readable medium storing instructions for use in characterizing lesions in radiology images that, when executed by one or more processors, cause the one or more processors to:
  perform a computer-based analysis comprising one or more of: advanced image analytics, machine learning, or artificial intelligence of a pathology image of a sample of a lesion of a subject in order to recognize tissue or cellular characteristics of the lesion, wherein the analysis produces a derived pathology image representative of the recognized tissue or cellular characteristics, co-registering a radiology image of the lesion and the derived pathology image;
  compute one or more radiology features for the radiology image of the lesion;
  determine correlations between the computed one or more radiology features and recognized tissue and/or cellular characteristics in the derived pathology image, by computing one or more features that are characteristic for a whole sample of the lesion from the derived pathology image and correlating the computed one or more radiology features and one or more features computed from the derived pathology image, wherein the correlating does not depend on co-registering the radiology image of the lesion and the derived pathology image; and
  characterize the lesion in the radiology image based on at least a subset of the one or more computed radiology features and the corresponding determined correlations.

13. The non-transitory computer readable medium of claim 12, storing further instructions to:
  characterize an area of the lesion in a same or different radiology image associated with the same subject based on at least a subset of the one or more computed radiology features for the area of the lesion and the determined correlations between the computed one or more radiology features and recognized tissue or cellular characteristics in the derived pathology image; and characterize a different lesion in a radiology image associated with the same or a different subject or the same lesion in a different radiology image associated with the subject based on at least a subset of the one or more radiology features computed for the different lesion from the radiology image of the same or the different subject or for the same lesion from the different radiology image of the subject and the corresponding determined correlations between the computed one or more radiology features and recognized tissue and/or cellular characteristics in the derived pathology image.

14. The non-transitory computer readable medium of claim 13, wherein the subset of the one or more radiology features is selected based on the strength of the corresponding determined correlations.

15. The non-transitory computer readable medium of claim 12, wherein the spatial resolution of the derived pathology image is adjusted to substantially match the spatial resolution of the radiology image(s).

16. The non-transitory computer readable medium of claim 12, wherein the co-registering is based on an automatic feature recognition or employs spatial information determined by an image-guided biopsy of the sample.

17. The non-transitory computer readable medium of claim 12, wherein determining the correlations further comprises selecting at least one area in the derived pathology image representing a particular recognized tissue or cellular characteristic and analyzing the computed one or more radiology features for a corresponding area in the co-registered radiology image.

18. The non-transitory computer readable medium of claim 12, wherein determining the correlations further comprises computing one or more features for at least one area from the derived pathology image and correlating the one or more features computed for the at least one area from the derived pathology image and the computed one or more radiology features for a corresponding area in the co-registered radiology image.

* * * * *